(12) United States Patent
Cipriano et al.

(10) Patent No.: US 9,861,545 B2
(45) Date of Patent: Jan. 9, 2018

(54) SYSTEM AND METHOD OF INFANT CARE CONTROL AND WORKFLOW

(71) Applicant: General Electric Company, Schenectady, NY (US)

(72) Inventors: James P. Cipriano, Ellicott City, MD (US); Lawrence G. Ten Eyck, Ellicott City, MD (US); Karen P. Starr, Monkton, MD (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/818,948

(22) Filed: Aug. 5, 2015

(65) Prior Publication Data
US 2015/0335510 A1 Nov. 26, 2015

Related U.S. Application Data

(63) Continuation of application No. 13/328,831, filed on Dec. 16, 2011, now abandoned.

(51) Int. Cl.
*A61G 11/00* (2006.01)
*G06F 19/00* (2011.01)

(52) U.S. Cl.
CPC ........ *A61G 11/009* (2013.01); *G06F 19/3406* (2013.01); *A61G 11/003* (2013.01); *A61G 11/004* (2013.01); *A61G 2203/16* (2013.01); *A61G 2203/20* (2013.01); *A61G 2203/30* (2013.01); *A61G 2203/46* (2013.01)

(58) Field of Classification Search
CPC .............. A61G 11/009; A61G 2203/16; A61G 2203/20; A61G 2203/46; A61G 11/003; A61G 11/004; A61G 2203/30; G06F 19/3406

USPC ................... 600/22, 301; 236/2, 91; 200/61; 119/304, 315, 311; 128/920; 237/3, 14; 435/303.1; D24/163
See application file for complete search history.

(56) References Cited

U.S. PATENT DOCUMENTS

| 4,640,368 | A | * | 2/1987 | Kittle ................... A01B 63/112 172/430 |
| 4,896,280 | A | | 1/1990 | Phillips |
| 4,936,824 | A | | 6/1990 | Koch et al. |
| 5,039,006 | A | * | 8/1991 | Habegger ............... F23N 5/242 236/1 G |
| 5,291,900 | A | | 3/1994 | Lowenstein |
| 5,376,761 | A | | 12/1994 | Koch et al. |

(Continued)

FOREIGN PATENT DOCUMENTS

DE 20310574 U1 3/2004

OTHER PUBLICATIONS

Sanyo, "Amorphous Silicon Solar Cells/Amorphous Phtotsensors", pp. 1-4, and 9-10, Nov. 2011.

*Primary Examiner* — Navin Natnithithadha
*Assistant Examiner* — Sunita Reddy
(74) *Attorney, Agent, or Firm* — Andrus Intellectual Property Law, LLP

(57) ABSTRACT

An infant care system creates a microenvironment about an infant patient. An environmental control device is operable to change an environmental condition within the microenvironment. An auxiliary sensor is operable to intermittently obtain auxiliary data. A processor operates the environmental control device based upon at least the intermittently obtained auxiliary data.

16 Claims, 3 Drawing Sheets

(56) References Cited

U.S. PATENT DOCUMENTS

| | | | |
|---|---|---|---|
| 5,474,517 A | 12/1995 | Falk et al. | |
| 5,498,229 A * | 3/1996 | Barsky | A61G 11/00 600/122 |
| 5,499,457 A | 3/1996 | Weiler et al. | |
| 5,730,355 A * | 3/1998 | Lessard | A61G 11/00 237/14 |
| 5,817,003 A | 10/1998 | Moll et al. | |
| 5,871,913 A | 2/1999 | Maddon et al. | |
| 5,971,913 A * | 10/1999 | Newkirk | A61F 7/00 600/22 |
| 6,213,935 B1 | 4/2001 | Mackin et al. | |
| 6,956,175 B1 | 10/2005 | Daly et al. | |
| 7,038,588 B2 | 5/2006 | Boone et al. | |
| 7,255,671 B2 | 8/2007 | Boone et al. | |
| 7,282,022 B2 | 10/2007 | Falk et al. | |
| 7,311,657 B2 | 12/2007 | Boone et al. | |
| 7,357,811 B2 | 4/2008 | Dykes et al. | |
| 7,364,539 B2 | 4/2008 | Mackin et al. | |
| 7,442,163 B2 | 10/2008 | Ten Eyck et al. | |
| 7,927,269 B2 | 4/2011 | Ten Eyck et al. | |
| 8,094,013 B1 * | 1/2012 | Lee | A61B 5/1116 340/539.15 |
| 2002/0044059 A1 | 4/2002 | Reeder et al. | |
| 2002/0143233 A1 * | 10/2002 | Donnelly | A61F 7/00 600/22 |
| 2002/0196141 A1 | 12/2002 | Boone et al. | |
| 2004/0170216 A1 | 9/2004 | Russak et al. | |
| 2004/0236174 A1 * | 11/2004 | Boone | A61G 11/006 600/21 |
| 2004/0236175 A1 | 11/2004 | Boone et al. | |
| 2005/0215844 A1 * | 9/2005 | Ten Eyck | A61B 5/02055 600/22 |
| 2008/0183029 A1 * | 7/2008 | Mackin | A61B 5/0002 600/22 |
| 2009/0149696 A1 | 6/2009 | Chilton, III | |
| 2010/0005675 A1 | 1/2010 | Gerster | |
| 2010/0042013 A1 | 2/2010 | Cuesta Frau et al. | |
| 2010/0057490 A1 * | 3/2010 | Kocis | G06F 19/345 705/2 |
| 2011/0273286 A1 | 11/2011 | Sklat | |
| 2012/0116050 A1 | 5/2012 | Muellen et al. | |
| 2012/0198715 A1 | 8/2012 | Eaton | |

\* cited by examiner

SYSTEM AND METHOD OF INFANT CARE CONTROL AND WORKFLOW

CROSS REFERENCE TO RELATED APPLICATION

This application is continuation of U.S. application Ser. No. 13/328,831, filed Dec. 16, 2011, which application was published on Jun. 20, 2013, as U.S. Publication No. US20130158339, which is incorporated herein by reference in its entirety.

BACKGROUND

The present disclosure is related to the field of infant care. More specifically, the present disclosure is related to systems and methods of infant care control and workflow.

Infants, and particularly neonates, require particular medical diligence and care. As a form of medical assistance, neonates are placed within a microenvironment that is designed to provide one or more environmental conditions that are advantageous to the neonate beyond the ambient conditions. Infant care stations provide this microenvironment for infant patients under the operation and control of a clinician upon observation of the condition of the infant patient.

BRIEF DISCLOSURE

An embodiment of an infant care station in accordance with one embodiment disclosed herein includes at least one physiological sensor disposed to connect to the patient. An auxiliary data sensor is operable by the user to obtain physiological data from the patient. A graphical display is operable to visually present data. A processor is communicatively connected to the at least one physiological sensor and the at least one auxiliary data sensor and the graphical display. The processor operates the graphical display to present a trend graph in conjunction with the intermittently obtained physiological data from the patient.

An infant care station in accordance with an embodiment as disclosed herein is operable to create a microenvironment about a patient. An environmental control device is operable to change an environmental condition within the microenvironment. An auxiliary sensor is operable by a user to intermittently obtain auxiliary data. A graphical display is operable to visually present data. A processor is communicatively connected to the auxiliary sensor, environmental control device, and the graphical display. The processor is selectively communicative with the auxiliary sensor. The processor operates the graphical display to present the intermittently obtained auxiliary data. The processor operates the environmental control device based upon at least the intermittently obtained auxiliary data.

In accordance with an embodiment of a method of caring for an infant patient, a microenvironment is provided for the infant with an infant care station. Environmental data is sensed from at least one environmental sensor disposed within the microenvironment. The microenvironment is controlled based upon the sensed environmental data. Physiological data is sensed from the infant in the microenvironment provided by the infant care station. An auxiliary sensor is selectively connected to the infant care station. Auxiliary data is intermittently obtained with the auxiliary sensor. The obtained auxiliary data is presented on a graphical display. The microenvironment is controlled based upon the obtained auxiliary data.

BRIEF DESCRIPTION OF THE DRAWINGS

The drawings illustrate the best mode presently contemplated of carrying out the invention. In the drawings.

DETAILED DISCLOSURE

Figure 1:
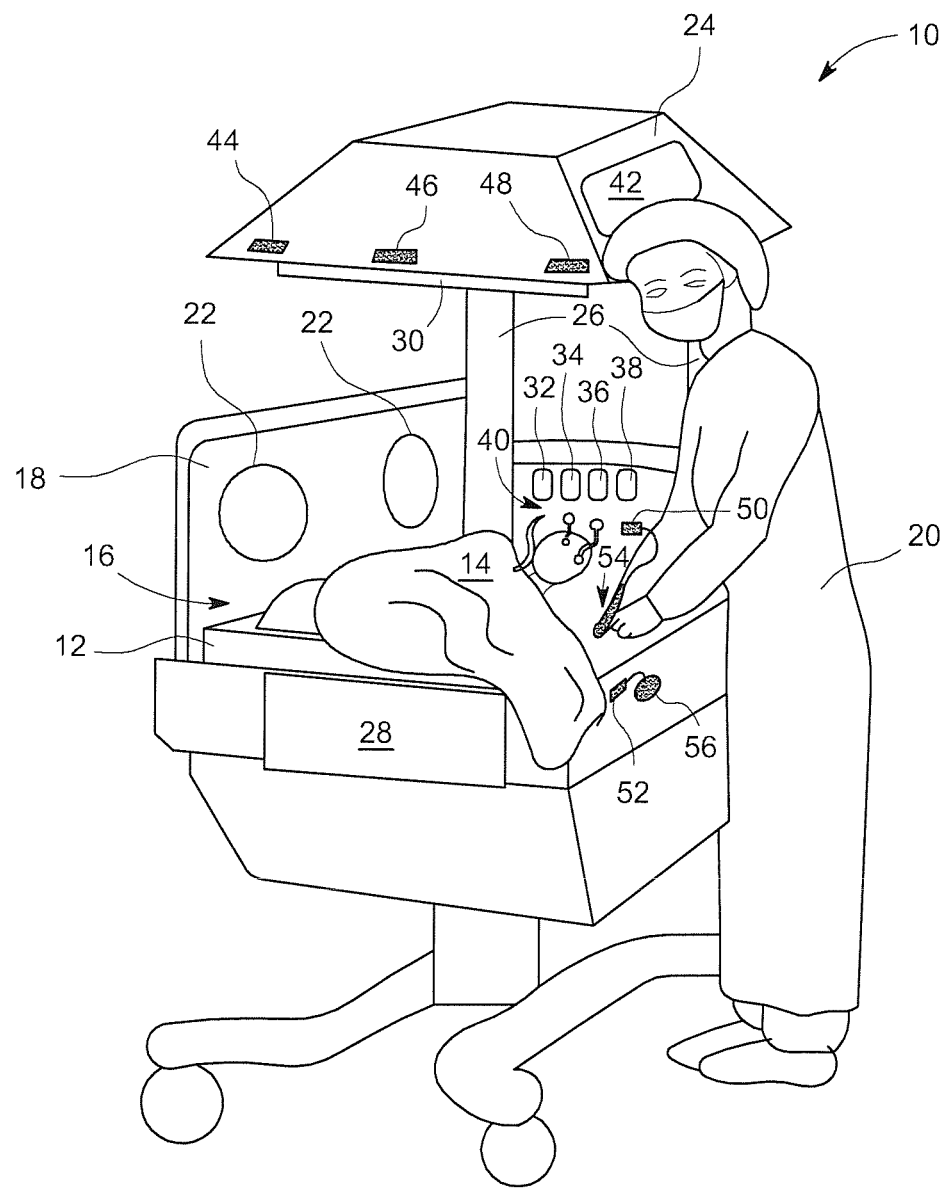
FIG. 1 is perspective view in accordance with an embodiment of an infant care station disclosed herein.

FIG. 1 is a perspective view of an embodiment of infant care station 10 in accordance with that disclosed herein. The infant care station 10 includes a generally horizontal surface 12 that is configured to support an infant patient 14. The infant care station 10 is generally any of a variety of devices that define a microenvironment 16 about the infant patient 14. Some non-limiting examples of the infant care station 10 may be an infant warmer, an incubator, or a hybrid warmer/incubator.

The infant care station 10 depicted in FIG. 1 is exemplarily a hybrid warmer/incubator. The microenvironment 16 is defined by at least one wall 18. The at least one wall 18 may be movable such as to permit the clinician 20 to have access to the infant patient 14. Alternatively, the wall 18 may include one or more arm ports 22 through which the clinician 20 may reach to access the infant patient 14. A canopy 24 is positioned above the microenvironment 16 and is movable along at least one rail 26. However, it will be understood that a variety of alternative mechanisms are available to one of ordinary skill in the art such as to secure the canopy 24 in a position movably above the microenvironment 16. The microenvironment 16 is therefore a space about the infant patient 14 that is defined by the infant care station 10. The infant care station 20, as discussed herein, operates to control one or more environmental conditions within the microenvironment 16. Non-limiting examples of environmental conditions include temperature, humidity, oxygen concentration, and light.

Embodiments of the infant care station 10 that operate as a warmer or a hybrid warmer/incubator include a convective heater 28. The convective heater 28 is operated by a processor (not depicted), as described further herein, of the infant care station 10 to warm ambient air and deliver the warm ambient air to the microenvironment 16 to control the temperature of the microenvironment 16 about the infant patient 14.

Embodiments of the infant care station 10 that are an incubator or a hybrid warmer/incubator include the canopy 24. A radiant warmer 30 is disposed in the canopy 24. The radiant warmer 30 operates to direct radiant heat energy at the infant patient 14 to provide effective warming and thermal management of the infant patient 14. Like the convective heater 28, the radiant warmer 30 is operated by the processor (not depicted) of the infant care station 10 in order to achieve the intended warming function of the infant patient 14. In some embodiments of the infant care station 10, both the convective heater 28 and the radiant warmer 30 are operated to maintain the temperature of the infant patient 14 and the microenvironment 16.

While not explicitly depicted in the infant care station 10 of FIG. 1, the infant care station 10 can control the environmental qualities of the microenvironment 16 in more ways than just the temperature of the microenvironment 16. Rather, embodiments of the infant care station 10, and as discussed in further detail herein, can control other environmental conditions of the microenvironment, including the oxygen concentration in the microenvironment 16, a humidity level within the microenvironment 16, and/or the lighting of the microenvironment 16. In such embodiments, the infant care station 10 can include a source of oxygen, exemplarily a cylinder of compressed oxygen gas, or a connection to a wall supply of oxygen in a medical care facility. Such oxygen from the oxygen supply can be applied to the microenvironment 16 through the convective heater 28. Furthermore, a humidifier (not depicted) can also provide humidity to the warmed medical gas (e.g. air or oxygen enriched air) supplied to the microenvironment 16 by the convective heater 28. Furthermore, one or more light sources (not depicted) in the canopy 24 can control the light in the microenvironment 16.

The infant care station 10 includes a plurality of sensors that are configured to monitor various conditions within the microenvironment. In accordance with the above disclosed environmental conditions of the microenvironment 16 that may be controlled by the infant care station 10, embodiments of the infant care station 10 may include a microenvironment temperature sensor 32, humidity sensor 34, oxygen sensor 36, and/or light sensor 38. It is to be understood that the disclosed temperature sensor 32, humidity sensor 34, oxygen sensor 36, and light sensor 38 may be located in various positions about the microenvironment 16, as would be recognized by one of ordinary skill in the art for these particular environmental conditions of the microenvironment 16. The sensed temperature, humidity, oxygen, and/or light from the respective sensors (32-38) are provided to the processor (not depicted) of the infant care station 10 and used by the processor to control the environmental conditions maintained within the microenvironment 16 about the infant patient 14.

In some embodiments as disclosed herein, the infant care station, through the processor operates to control the environmental conditions of the microenvironment in a variety of ways. In one embodiment, the processor operates as an environmental control device in response to one or more of the environment sensors. In another embodiment, the microenvironment is controlled to maintain set values for environmental conditions in the microenvironment. These are both of closed loop control of the microenvironment. In an alternative embodiment, the environmental conditions of the microenvironment are controlled in an open loop control wherein an environmental control device (e.g. heater, light source, oxygen source, or humidifier) is operated at a fixed level independent from any measured conditions. In a non-limiting example, the convective heater could be operated at 50% or 75% of maximum strength.

The infant care station 10 further includes at least one physiological sensor 40 that is operable to obtain physiological data from the infant patient 14. While a variety of physiological sensors may be used in various embodiments, as recognized by one of ordinary skill in the art, two non-limiting examples of such physiological sensors includes an electrocardiographic (ECG) electrode or a blood oxygenation (SpO2) sensor. In another exemplarily embodiment, the physiological sensor 40 is a thermometer or other temperature sensor that may be configured to secure to the skin of the infant patient 14. Embodiments of the infant care station 10 include a plurality of physiological sensors 40 in the manner as described above, or as otherwise recognized by one of ordinary skill in the art.

In embodiments, the temperature sensor 32, humidity sensor 34, oxygen sensor 36, light sensor 38, and physiological sensor 40 all operate in a continuous or generally continuous manner to monitor conditions of the microenvironment 16 and/or of the infant patient 14. The continued or generally continuous measurements are provided to the aforementioned processor of the infant care station 10 and may be used by the processor to operate one or more of the convective heaters 28, radiant warmer 30, or other components of the infant care station.

In some embodiments, the infant care station 10 further includes a graphical display 42. The graphical display 42 is operated by the processor to present information regarding the microenvironment 16 and the infant patient 14, or other operations of the infant care station 10. In embodiments, the processor uses the information obtained from the temperature sensor 32, humidity sensor 34, oxygen sensor 36, light sensor 38, and physiological sensor 40 in order to present some or all of this data to the clinician 20 on the graphical display 42. In still further embodiments, the graphical display 42 is touch-sensitive display, such that the graphical display 42 also operates as a user input device. In alternative embodiments, a separate user input device (not depicted) is provided on the infant care station 10. While the graphical display 42 is depicted as being located on the canopy 24, it is to be recognized that in alternative embodiments, the graphical display 42 and any associated user input device may be located in other locations on the infant care station 10.

The infant care station 10 is further configured with one or more auxiliary data sensors that operate in addition to the temperature sensor 32, humidity sensor 34, oxygen sensor 36, light sensor 38, and physiological sensor 40 as described above.

Embodiments of the infant care station 10 may include one or more external environment sensors. These external environment sensors may exemplarily be one or more of an external temperature sensor 44, ambient light sensor 46, and draft sensor 48. These external environment sensors are examples of auxiliary data sensors that monitor the conditions outside of the infant care station 10, and more specifically, the environmental conditions outside of the microenvironment 16. While the external temperature sensor 44, ambient light sensor 46, and draft sensor 48 are depicted as being located on the canopy 24, it is to be recognized that in alternative embodiments, these sensors may be located in other positions on the infant care station outside of the microenvironment 16. The external temperature sensor 44 is exemplarily, but not limited to, a thermometer. The ambient light sensor 46 is exemplarily, but not limited to, a photovoltaic cell and the draft sensor 48 is exemplarily, but not limited to, an anemometer. The environmental data obtained from the external environment sensors is further provided to the processor (not depicted) of the infant care station 10 such that the infant care station 10 uses this external environment data to further manage the microenvironment 16. Such management of the environmental conditions within the microenvironment 16, may control the operations of the convective heater 28 or radiant warmer 30 in response to a differential temperature between the microenvironment temperature and the temperature measured outside of the microenvironment. Further, these responses can be provided by the processor and to mitigate the detection of a draft about the infant care station 10, including, but not limited to, management of the convective heater 28, radiant warmer 30, or lowering of the canopy 24.

Embodiments of the infant care station 10 further include at least one microenvironment data connection 50, and/or at least one external data connection 52. Such data connections 50 and 52 are exemplarily a USB or similar data connection; however, it will be recognized that alternative types of data connections may be used within the scope of the present disclosure. Non-limiting examples of other data connections can include a device as disclosed further herein integrally connected to the infant care station, or a wireless, exemplarily an RF data connection.

The microenvironment data connection 50 and the external data connection 52 provide further connection points for at least one auxiliary data sensor, which may exemplarily be a physiological sensor, including, but not limited to, a thermometer probe 54 or an electronic tape measure 56; however, it will be recognized that alternative physiological sensors may be used in other embodiments. The temperature probe 54 and electronic tape measure 56 are exemplarily physiological sensors that are intermittently used and further require active operation by the clinician 20 to obtain the physiological data. Exemplarily, the temperature probe 54 is a digital thermometer that is used by the clinician 20 to intermittently obtain an axillary temperature of the infant patient 14. While the infant care station 10 may include a temperature sensor as described above that is secured to the skin of the patient and provides a continuous or generally continuous measurement of patient skin temperature, other more specific intermittent temperature measures can be clinically important, and such physiological data values can be intermittently updated for the infant patient 14 with clinician measurements. The advantage of the temperature probe 54 being connected to the infant care station 10 through the microenvironment data connection 50 is that the temperature probe 54 remains in the microenvironment 16 and its use therefore can be performed with minimal impact on the microenvironment 16. Furthermore, the digital temperature obtained by the temperature probe 54 can be directly provided to the processor (not depicted) of the infant care station 10 such that the processor can store the measured axillary temperature, and such axillary temperature can be used in the operation of the infant care station 10. It is to be further recognized, that the temperature probe 54 may be alternatively used by the clinician 20 to measure temperature at a different location of the infant patient 14, including, but not limited to, a rectal thermometer.

The electronic tape measure 56 is shown as being exemplarily connected to the external data connection 52; however, it is to be recognized that this is intended to be merely exemplary of the fact that the infant care station 10 may include data connections within and external to the microenvironment, and that the physiological sensors may be connected to any of such data connections. The electronic tape measure 56 enables the clinician 20 to intermittently obtain anatomical measurements of the infant patient 14, including, but not limited to, patient length and head circumference. The electronic tape measure 56 records these measurements as a digital value and provides these digital values to the processor of the infant care station 10 through the data connection 52.

Figure 2:
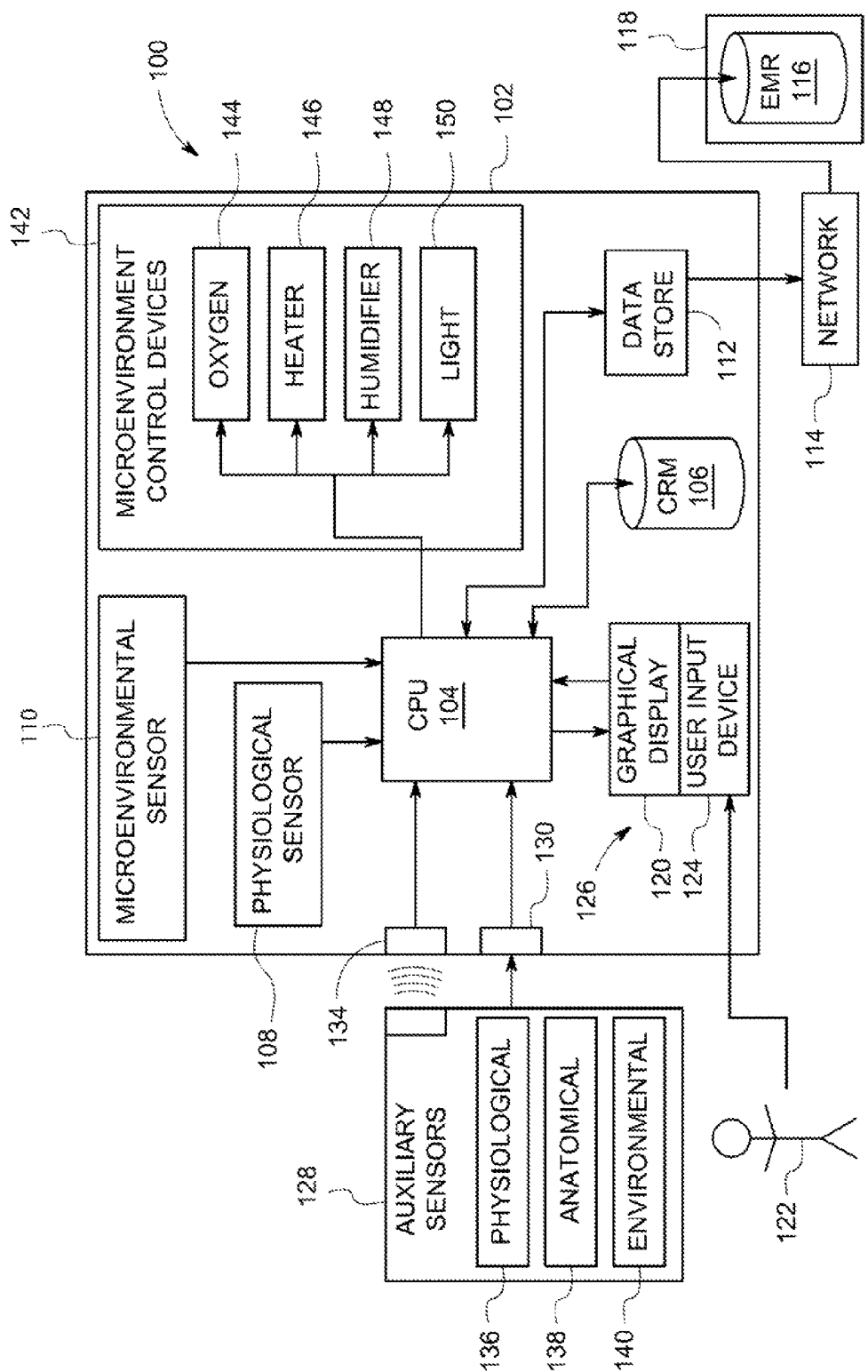
FIG. 2 is a system diagram in accordance with an embodiment of an infant care system as disclosed herein.

FIG. 2 is a system diagram in accordance with an embodiment of an infant care system 100. The infant care system 100 includes an infant care station 102, a non-limiting embodiment of which is depicted and described above with respect to FIG. 1. The infant care station 102 includes a processor 104 which is exemplarily a central processing unit (CPU) or other type of controller as known in the art. Computer readable code is stored either locally at the processor 104, or the processor 104 is communicatively connected to a non-transient computer readable medium 106, exemplarily non-volatile memory, that stores the computer readable code that when accessed and executed by the processor 104, causes the processor 104 to carry out the functions and operations as disclosed herein. As non-limiting examples to the computer readable code stored on the computer readable medium 106, such computer readable code may include data analysis algorithms for collecting, processing, and outputting data received by the processor 104, and operational or control algorithms used by the processor to control the functions of the infant care station 102.

As disclosed above with respect to FIG. 1, the infant care station 102 can include at least one physiological sensor 108 that obtains physiological data from the infant patient and at least one microenvironmental sensor 110 configured to obtain environmental data from the microenvironment provided by the infant care station 102. The physiological sensor 108 and the microenvironmental sensor 110 operate continuously or generally continuously to provide physiological and environmental data to the processor 104. The processor 104 uses at least one analysis algorithm, exemplarily obtained from the computer readable medium 106 in order to process the physiological data and the environmental data. The processed physiological data and environmental data is provided to a data store 112, which is exemplarily volatile or non-volatile computer memory that locally stores the processed data at the infant care station 102 for further use of the processed data at the infant care station 102 as described herein. The processed data at the data store 112 may exemplarily be physiological data and/or environmental data after basic processing such as digitization, filtering, and other signal processing or otherwise may be processed data that has been processed by more advanced algorithms such as to refine the saved physiological data or environmental data into specified values.

The data store 112 is further connected externally of the infant care station 102 to a data network 114. The data network 114 is exemplarily the network of the medical care facility within which the infant care station 102 is used. The data network 114 provides a communicative connection between the infant care station 102 and an electronic medical record (EMR) 116 of the infant patient that may be stored on an EMR server 118 of the medical care facility. Thus, from the data store 112, the infant care station 102 can push the processed physiological and environmental data out to be recorded at the remotely stored EMR of the infant patient 116, while retaining some or all of the processed data locally at the data store 112 for later access and local use by the processor 104 and the infant care station 102.

The analysis algorithms as applied by the processor 104 to the attained physiological data from the physiological sensor 108 and the obtained environmental data from the microenvironmental sensor 110 further produce processed data that is suitable for presentation by a graphical display 120 of the infant care station 102. The presented processed data can include instantaneous or moving average values of the physiological data and environmental data, but furthermore the processor 104 can operate the graphical display 120 to present trends of changes in the physiological data and/or environmental data over time. Such trend graphs may require the processor 104 to access the locally stored processed data at the data store 112. The graphical display 120 presents the processed data to the clinician for review and analysis of the conditions of the infant patient and the microenvironment by the clinician 122. The clinician 122 enters further data and commands to the infant care station 102 through a user input device 124, which data and commands are provided back to the processor 104. The graphical display 120 and user input device 124 may be exemplarily referred to as a user interface 126, and as such may be provided by a separate device, or may be provided by a combined device, exemplarily a touch sensitive display.

As described above with respect to FIG. 1, one or more auxiliary sensors 128 are communicatively connected to the processor 104. In one embodiment, the one or more auxiliary sensors are communicatively connected to the processor 104 through one or more data connections 130. In one embodiment, the data connection 130 is a universal service bus (USB) formatted connector that receives a similar adapter as connected to the auxiliary sensor 128. It will be recognized by one of ordinary skill in the art that alternative types of removably securable physical data connections may be used within the present disclosure. In still further embodiments, one or more auxiliary sensors 128 are hard wired to the infant care station 102 and processor 104, such that the auxiliary sensors 128 are formed as an integral part of the infant care station 102. In a still further embodiment, the auxiliary sensors 128 further include a wireless communication transmitter, exemplarily operating the Bluetooth RF wireless communication protocol and transmit the obtained data to a receiver 134 that is communicatively connected to the processor 104.

The one or more auxiliary sensors 128 obtain data beyond that which is obtained by the physiological sensor 108 and environmental sensor 110. Such auxiliary sensors include, but are not limited to, a physiological auxiliary sensor 136, exemplarily a thermometer; an anatomical auxiliary sensor 138, exemplarily an electronic tape measure; or an external environmental sensor 140, exemplarily an external temperature sensor, ambient light sensor, or draft sensor.

In embodiments, the at least one auxiliary sensor 128 is configured to intermittently obtain the auxiliary data obtained by the specific sensor. In still further embodiments, the auxiliary sensor 128 is configured to be operable by the clinician 122 in order to acquire the auxiliary data. In a non-limiting example, auxiliary sensor 128 may be a digital thermometer that is used by the clinician 122 to obtain an axillary or rectal temperature of the infant patient and the measured digital temperature is communicated from the auxiliary sensor 128 to the processor 104. In a still further embodiment, the auxiliary sensor 128 is an electronic tape measure and the clinician 122 operates the electronic tape measure to measure a length and/or a head circumference of the infant patient and such electronically obtained anatomical measurements are communicated to the processor 104.

The processor 104 receives the auxiliary data from the at least one auxiliary sensor 128 and processes the auxiliary data according to one or more analysis algorithms as obtained from the computer readable medium 106, or stored locally at the processor 104. In embodiments, the processor 104 creates a time stamp that is associated to the received auxiliary data. The processor 104 sends the processed auxiliary data to the data store 112 for local storage of the auxiliary data, along with the time stamp, if available. The data store 112 also pushes the auxiliary data out to the network 114 for storage at the infant patient EMR 116. The processor 104 further operates the graphical display 120 in order to modify the trend graphs of the physiological data obtained from the physiological sensor 108 and the environmental data obtained from the microenvironmental sensor 110 in order to overlay the obtained auxiliary data on the trend presentations. The incorporation of the auxiliary data values into the trend graphs presented by the graphical display 20, further may use the time stops created at each receipt of auxiliary data. With the time stamps, the processor 104 can cause the auxiliary data values to be presented with temporal indications relative to the trend graphs on the graphical display 120.

In a non-limiting example, the processor 104 may operate the graphical display 120 to present a trend of the microenvironment temperature as obtained by the microenvironmental sensor 110 exemplarily over the previous seven days. Within the graphical display 120, the processor 104 overlays the intermittently acquired auxiliary data of measured patient axillary temperature and the intermittently obtained external temperature data. Therefore, the clinician 122 observing the presentation of this data on the graphical display 120 can relate the trends of the continuously or generally continuously obtained microenvironment temperature with the intermittently obtained axillary temperature and external temperature. In an alternative example, the continuously monitored skin temperature of the infant patient obtained by the physiological sensor 108 can be trended over exemplarily the previous fourteen days and the intermittently obtained auxiliary data of the infant patient's length, head size, and axillary temperature can be overlaid over the patient's skin temperature trend graph. The above examples are intended to be merely exemplary of the types of presentations of data that may occur within the scope of the present disclosure, and are not intended to be limiting upon the scope of the disclosure.

As described above, the infant care station 102 includes one or more microenvironment control devices 142 that are operated to control environmental conditions maintained within the microenvironment of the infant care station 102. Embodiments of the infant care station 102 and infant care system 100, as disclosed herein, further use the auxiliary data to provide refined operation of the microenvironment control devices 142. The microenvironment control devices 142 exemplarily include an oxygen source 144, a heater 146, which may exemplarily be one or more of a convective heater and a radiant warmer, a humidifier 148, and/or a light source 150. The processor 104 operates the microenvironment control devices 142 which account for the additionally collected auxiliary data. More specifically, the auxiliary data is used by the control algorithms executed by the processor 104 in operating the microenvironment control devices 142.

In one non-limiting embodiment, the auxiliary data that is intermittently obtained is the axillary temperature of the patient. The intermittently obtained axillary temperature is used by the processor 104 to modify the control algorithm used to operate the heater 146 to control the temperature of the microenvironment. In a further non-limiting embodiment, the auxiliary data is a length and a head circumference of the infant patient, and the processor 104 uses the obtained measurement auxiliary data to modify the control algorithms exemplarily the control algorithms used to operate the oxygen source 144 for providing oxygen to the microenvironment. In another non-limiting embodiment, the auxiliary data is an external temperature or a draft detection outside of the microenvironment and the auxiliary data is used by the processor 104 to modify the control algorithm used to operate the heater 146 or humidifier 148 in a manner such as to control the environmental conditions within the microenvironment. In one such embodiment, the differential temperature between a target temperature of the microenvironment and a measured external temperature outside of the microenvironment may exemplarily be used by the processor 104 in controlling the operation of the heater 146. In a still further non-limiting embodiment, the auxiliary data may be an ambient light intensity external to the microenvironment and this auxiliary data is used by the processor 104 to modify the control algorithms used by the processor 104 to operate the light source 150 to illuminate the microenvironment. Similar to the example above, the differential in the ambient and the target illumination may be used by the processor 104 in order to modify the operation of the light source 150 or to implement or recommend a light control response, exemplarily tinting or covering the microenvironment.

In a still further embodiment, the auxiliary data can be used either independently, or in conjunction with other data from the infant patient's EMR or the physiological sensor, to classify the infant patient, or make a recommendation as to patient condition. In a non-limiting example, one or more of the patient's auxiliary temperature, head circumference, and length can be used to determine if the infant patient is a feeder/grower or an extremely low birth weight (ELBW) patient.

In still further embodiments, the processor 104 does not automatedly modify the operation of one or more microenvironment control devices 142 based upon the received auxiliary data from the at least one auxiliary sensor 128. Rather, the processor 104 may operate the graphical display 120 in order to present one or more recommendations for modifications to the operation of the microenvironment control devices 142 to be selected or enacted by the clinician 122. The processor 104 may operate the graphical display 120 to identify the recommendations and/or provide a user interface 126 within which the clinician 122 can make such selections or modifications to the operation of the microenvironment control devices 142. The processor 104, exemplarily through the data store 112, can further push recommended and/or enacted images to the operation of the microenvironment control devices including, but not limited to a time stamped notation of such operational changes.

In still further embodiments, the processor 104 operates the user interface 126 in order to prompt or otherwise solicit the clinician 122 to enter additional information with the user input device 124 such as to perform noting and charting tasks at the bedside of the infant patient. The user interface 126 can be operated by the processor 104 to receive notes and other inputs, including time stamps of other events that occur in the treatment of an infant patient. Non-limiting examples of such events that can be noted in this manner include diaper changes, bed linen changes, kangaroo care start and end times, phototherapy start and end times, distribution of meds, and feeding events. Still further examples of the types of events that can be documented by the clinician through the user interface of the infant care station 102 include tests performed and/or the results of such tests. Non-limiting examples of such tests can be an APGAR score or a hearing test. The processor 104 receives these additional data inputs that are indicative of the treatment or condition of the infant patient and can further use these inputs to control the operation of the microenvironment control devices, and can push the entered inputs to the network 114 for storage on the EMR of the infant patient 116. In still further embodiments, the processor 104 can access the information stored on the EMR of the infant patient 116 through the network 114 and present the accessed patient data to the clinician with the user interface 126 and the clinician 122 can add, delete, and edit information within the infant patient's EMR, such that the clinician 122 can perform charting and data entry tasks at the infant patient's bedside using the infant care station 104.

Figure 3:
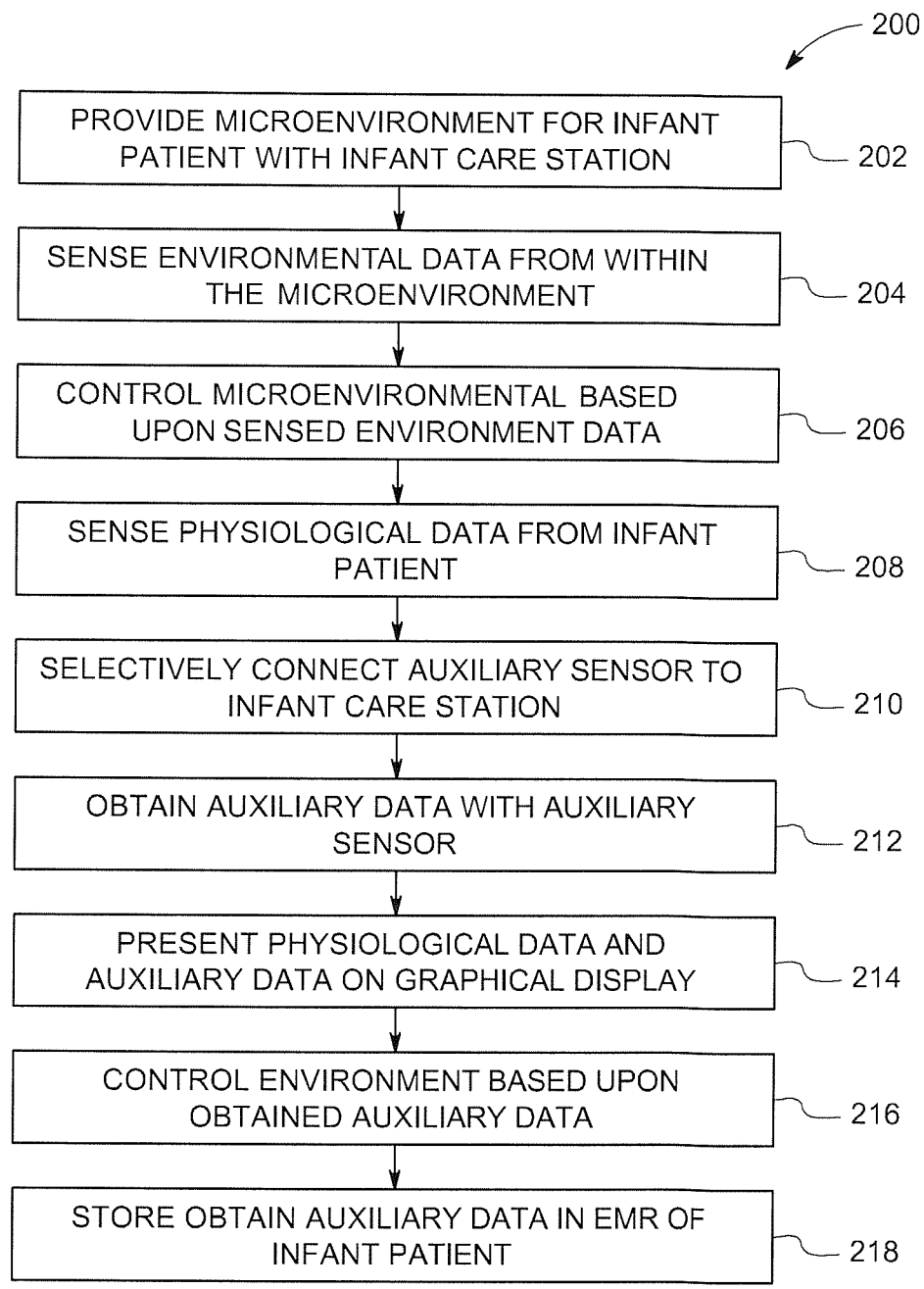
FIG. 3 is a flow chart of a method in accordance with the method of caring for an infant as disclosed herein.

FIG. 3 is a flow chart in accordance with an embodiment of a method 200 of providing care for an infant. The method starts at 202 where a microenvironment is provided for the infant patient with an infant care station. Embodiments of the infant care station that may be used to provide the microenvironment are disclosed above with respect to FIGS. 1 and 2. The infant patient is disposed within the microenvironment provided by the infant care station in order to receive the therapeutic support provided by such a microenvironment.

Next, environmental data is sensed from at least one environmental sensor that is disposed within the microenvironment. As disclosed above, any of a variety of environmental sensors may be used, including, but not limited to, an oxygen sensor, a thermometer, a humidity sensor, or a light sensor. One or more of these environmental sensors can be disposed within the microenvironment in order to sense environmental data that is representative of an environmental condition within the microenvironment.

At 206, the microenvironment as provided by the infant care station is controlled based upon the sensed environmental data of the at least one environmental sensor. The infant care station uses the sensed environmental data to control the operation of one or more environmental control devices in order to achieve or maintain a target environmental condition within the microenvironment.

At 208, physiological data is sensed from the infant patient by the infant care station while the infant patient is in the microenvironment provided by the infant care station. The physiological data sensed from the infant may include an infant skin temperature, an infant ECG, or an infant SpO2, although these are intended to be merely exemplarily and not intended to be limiting on the scope of physiological data that can be sensed from the infant patient. In some embodiments, the physiological data is sensed continuously or generally continuously from the infant patient when the infant patient is in the microenvironment provided by the infant care station.

Next, an auxiliary sensor is selectively connected to the infant care station at 210. As disclosed above, the auxiliary sensor can be any of a variety of physiological, anatomical, or environmental sensors and can be selectively connected to the care station by a physical or wireless communicative connection. At 212, the auxiliary sensor is used to intermittently obtain auxiliary data. In some embodiments, the obtained auxiliary data is physiological data, exemplarily an axillary temperature, anatomical data, exemplarily patient length, or environmental data, exemplarily external temperature outside of the microenvironment. The auxiliary sensor intermittently obtains the auxiliary data such as by selective operation of the auxiliary sensor by a clinician. As such, some embodiments of the auxiliary sensor may require the manipulation or use by the clinician in order to obtain the auxiliary data, such as is with a thermometer or an electronic tape measure.

Next, at 214 the sensed physiological data from 208 and the obtained auxiliary data from 212 are presented on a graphical display. As disclosed above, in one embodiment, the continuously or generally continuously sensed physiological data from 208 is presented as a trend or graph over time, while the intermittently obtained auxiliary data is presented as individual measurement values as obtained in points in time along the graph or trend of the sensed physiological data.

At 216, the infant care station operates to control the microenvironment provided by the infant care station based upon the obtained auxiliary data. As noted above, the intermittently obtained auxiliary data can be used by the infant care station to modify the way in which one or more of the microenvironment control devices are operated such as to modify one or more of the environmental conditions within the microenvironment and that such modifications can be made in response to the intermittently obtained auxiliary data. In one non-limiting example, a newly obtained value of the auxiliary data is used to replace a previously obtained value for the auxiliary data used in an algorithm executed by a processor to operate a device that controls an environmental condition of the microenvironment.

At 218, the infant care station operates in connection with an information network in order to store the obtained auxiliary data in the electronic medical record (EMR) of the infant patient. By directly causing the auxiliary data to be recorded in the infant patient's EMR, the infant care station can facilitate the maintenance of proper and accurate medical records of the infant patient during the treatment and care of the infant patient.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of caring for an infant, the method comprising:
    providing a microenvironment for the infant with an infant care station having an environmental control device operable to change an environmental condition within the microenvironment;
    sensing environmental data from at least one environmental sensor disposed internal the microenvironment, wherein the environmental data is internal environmental data collected from inside the microenvironment;
    controlling the microenvironment with the environmental control device to maintain a target environmental condition within the microenvironment based upon the internal environmental data;
    obtaining auxiliary data with an auxiliary sensor, the auxiliary sensor comprises an external environmental sensor disposed external to the microenvironment and the auxiliary data comprises external environmental data collected from outside of the microenvironment; and
    controlling the microenvironment with the environmental control device to maintain the target environmental condition within the microenvironment based upon the external environmental data.

2. The method of claim 1, wherein the external environmental sensor comprises at least one of an ambient light sensor, a draft sensor, and an external temperature sensor.

3. The method of claim 1, wherein the auxiliary sensor comprises an anatomical sensor.

4. The method of claim 3, wherein the anatomical sensor is an electronic tape measure, the auxiliary data comprises patient length or head circumference and the environmental control device operates an oxygen source to adjust the amount of oxygen provided to the microenvironment.

5. The method of claim 1 wherein the auxiliary sensor comprises at least one of a physiological sensor and an anatomical sensor and the auxiliary data comprises at least one of physiological data and anatomical data.

6. The method of claim 1, further comprising:
    continuously obtaining physiological data from the infant, with a physiological sensor in the microenvironment provided by the infant care station; and
    presenting a trend graph of at least one of the environmental data and the physiological data in conjunction with the auxiliary data.

7. The method of claim 1, further comprising:
    sensing physiological data from the infant in the microenvironment provided by the infant care station; and
    presenting the physiological data on a graphical display.

8. The method of claim 1, further comprising:
    storing the auxiliary data in an electronic medical record (EMR) of the infant.

9. A method of caring for an infant, the method comprising:
    providing an infant care station comprising:
        an environmental control device that operates to change an environmental condition within a microenvironment;
        at least one internal environmental sensor disposed within the microenvironment;
        an auxiliary sensor; and
        a processor communicatively connected to the auxiliary sensor, the at least one internal environmental sensor, and the environmental control device;
    providing the microenvironment for the infant with the infant care station;
    sensing internal environmental data from the at least one internal environmental sensor disposed within the microenvironment;
    maintaining a target environmental condition within the microenvironment with the environmental control device based upon the internal environmental data;
    obtaining auxiliary data with the auxiliary sensor; and
    changing an operation of the environmental control device to maintain the target environmental condition within the microenvironment with the environmental control device based upon the auxiliary data.

10. The method of claim 9, wherein the microenvironment is defined about the infant by a generally horizontal surface configured to support the infant, a canopy positioned above the generally horizontal surface, and at least one wall.

11. The method of claim 10, wherein the auxiliary sensor is an external environmental sensor located exterior of the microenvironment and the auxiliary data is external environmental data, further comprising:
    obtaining external environmental data from outside of the microenvironment.

12. The method claim 11, wherein the external environmental sensor comprises a light sensor located on an exterior surface of the infant care station directed away from the microenvironment, the target environmental condition is a light intensity and the environmental control device is a light source that maintains the target environmental condition, which is a light intensity within the microenvironment.

13. The method claim 11, wherein the external environmental sensor is a draft sensor located on an exterior surface of the infant care station.

14. The method of claim 13, wherein the environmental control device is selected from a humidifier and a movable canopy.

15. An infant care station comprising:
    a microenvironment configured to receive an infant patient, the microenvironment defined by at least a generally horizontal surface configured to support the infant patient, a canopy positioned above the generally horizontal surface, and at least one wall;

an internal environmental sensor located within the microenvironment, the internal environmental sensor configured to obtain internal environmental data from within the microenvironment;

an environmental control device configured to maintain a target light intensity within the microenvironment based upon the internal environmental data; and a light sensor located on an exterior surface of the canopy, the light sensor configured to obtain a light intensity from outside the microenvironment;

wherein the environmental control device is a light source or the canopy and operates in response to the light intensity to maintain the target environmental condition within the microenvironment.

16. An infant care station comprising:

a microenvironment configured to receive an infant patient, the microenvironment defined by at least a generally horizontal surface configured to support the infant patient, a canopy positioned above the generally horizontal surface, and at least one wall;

an internal environmental sensor located within the microenvironment, the internal environmental sensor configured to obtain internal environmental data from within the microenvironment;

an environmental control device configured to maintain a target environmental condition within the microenvironment based upon the internal environmental data, the target environmental condition comprising at least one of oxygen concentration, temperature, humidity, and light intensity; and an external environmental sensor located external to the microenvironment, the external environmental sensor configured to obtain external environmental data from outside the microenvironment, wherein the external environmental sensor is a draft sensor located on an exterior surface of the canopy;

wherein the environmental control device is selected from a heater, a humidifier, and a position of the canopy, and the environmental control device changes operation in response to the external environmental data to maintain the target environmental condition within the microenvironment.

* * * * *